(12) United States Patent
Ueno et al.

(10) Patent No.: US 7,504,492 B2
(45) Date of Patent: Mar. 17, 2009

(54) RNA POLYMERASE III PROMOTER, PROCESS FOR PRODUCING THE SAME AND METHOD OF USING THE SAME

(76) Inventors: Hiroyuki Ueno, 18-14-402, Minamisuita 5-chome, Suita-shi, Osaka 564-0043 (JP); Koichi Yokota, 2-203, Mozunishino-cho, Sakai-shi, Osaka 591-8033 (JP); Shigeki Higashiyama, 357-6, Yokogawara, Toon-shi, Ehime 791-0203 (JP)

( * ) Notice: Subject to any disclaimer, the term of this patent is extended or adjusted under 35 U.S.C. 154(b) by 232 days.

(21) Appl. No.: 10/545,946

(22) PCT Filed: Feb. 16, 2004

(86) PCT No.: PCT/JP2004/001665

§ 371 (c)(1),
(2), (4) Date: Aug. 17, 2005

(87) PCT Pub. No.: WO2004/074474

PCT Pub. Date: Sep. 2, 2004

(65) Prior Publication Data

US 2006/0253911 A1    Nov. 9, 2006

(30) Foreign Application Priority Data

Feb. 19, 2003    (JP) .............................. 2003-040965

(51) Int. Cl.
*C07H 21/04* (2006.01)
*C12P 21/06* (2006.01)
(52) U.S. Cl. .................................... 536/24.1; 536/23.1
(58) Field of Classification Search ....................... None
See application file for complete search history.

(56) References Cited

U.S. PATENT DOCUMENTS 6,632,980 B1 * 10/2003 Yadav et al. ................. 800/278
2004/0002077 A1 * 1/2004 Taira et al. ..................... 435/6

FOREIGN PATENT DOCUMENTS

WO    WO 01/11058    2/2001
WO    WO 02/83897    10/2002

OTHER PUBLICATIONS

Bernués et al. (1993) EMBO J. 12:3573-3585.*
H. Hasuwa et al.; "Small interfering RNA and gene silencing in transgenic mice and rats", FEBS Letters, 2002, vol. 532, No. 1-2, pp. 227-230.
PJ. Paddison et al.; Short hairpin RNAs (SnRNAs), induce sequence-specific silencing in mammalinan cells, Genes Dev., 2002, vol. 16, No. 8, pp. 948-958.

* cited by examiner

*Primary Examiner*—David Guzo
*Assistant Examiner*—Catherine S Hibbert
(74) *Attorney, Agent, or Firm*—Westerman, Hattori, Daniels & Adrian, LLP.

(57) ABSTRACT

The present invention provides an RNA polymerase III promoter characterized in that a part of its sequence is substituted with a sequence capable of undergoing specific DNA recombination by Cre recombinase in such a manner functions of PSE and a TATA box are not impaired. This RNA polymerase III promoter can be used in a RNAi induction method with the condition that RNAi molecules to be used in analyzing gene function can be induced at an arbitrary point of time or only in a specific tissue (organ).

1 Claim, 15 Drawing Sheets

Figure 1

(A) H1 promoter sequence (SEQ ID NO:2)

```
     -100        -90        -80        -70        -60
     aatat ttgca tgtcg ctatg tgttc tggga aatca ccata aacgt gaaat
           Octamer            Staf binding site                PSE
     -50        -40        -30        -20        -10        +1
     gtctt tggat ttggg aatct tataa gttct gtatg agacc actct ttccc A
                             TATA
```

(B) loxP sequence (SEQ ID NO:3)

```
     1     5    10    15    20    25    30
     ATAACTTCGTATA ATGTATGG TATACGAAGTTAT
```

(C) RH-loxP promoter sequence (SEQ ID NO:4)

```
     -100        -90        -80        -70        -60
     aatat ttgca tgtcg ctatg tgttc tggga aatca ccata aacgt gaaat
           Octamer            Staf binding site                PSE
     -50        -40        -30        -20        -10        +1
     gtctt tggat tATAA CTTCG TATAA TGTAT GGTAT ACGAA GTTAT ttccc A
                             TATA
```

Figure 3
Fluorescent field
pcDNA3.1
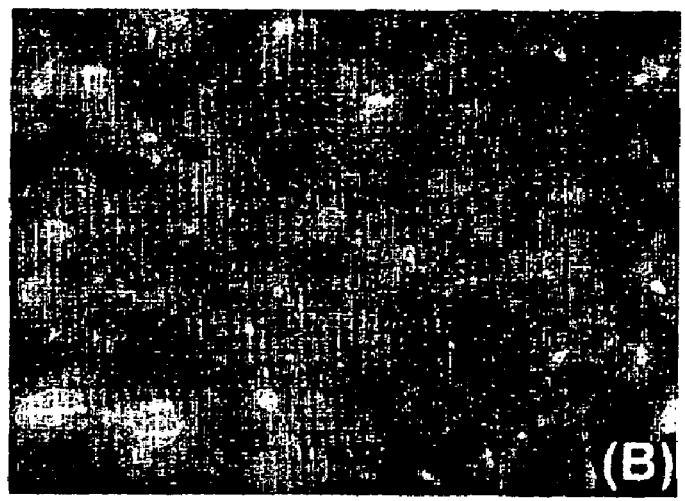
(B)
pUNO126 (H1)
(E)
pUNO137 (RH-loxP)
(H)

Figure 7

```
(SEQ ID NO:5) pUNO147 :TATACGAAGTTATTTCCC CTGCA GGTCG ACTCT AGAGG ATCCC CGGGA ATTCA
(SEQ ID NO:6) pUNO149 :TATACGAAGTTATTTCCC AGCTC TTTCT GGCTG CAGTT TTCAA GAGAA ACTGC
                                              +1 pUNO147 :GACAT GATAA GATAC ATTGA TGAGT TTGGA
pUNO149 :AGCCA GAAAG AGCTT TTTTG GATCT GGCCG (SEQ ID NO:7) pUNO148 :TATACGAAGTTATTTCCC CTGCA GGTCG ACTCT AGAGG ATCCC CGGGA ATTCA
(SEQ ID NO:8) pUNO150 :TATACGAAGTTATTTCCC ACGGC CACAA GTTCA GCGTG TTCAA GAGAC ACGCT
                                              +1 pUNO148 :GACAT GATAA GATAC ATTGA TGAGT TTGGA
pUNO150 :GAACT TGTGG CCGTT TTTTG GATCT GGCCG
```

Mice      WT

Plasmid      -

Mice        eGFP
Plasmid        -

Mice          eGFP
Plasmid    pUNO129

Mice       eGFP
Plasmid    pUNO148+pCre

RNA POLYMERASE III PROMOTER, PROCESS FOR PRODUCING THE SAME AND METHOD OF USING THE SAME

TECHNICAL FIELD

The present invention relates to a novel RNA polymerase III promoter, a method for producing the same and a method of using the same. More specifically, the present invention relates to an RNA polymerase III promoter that is characterized in that a part of its sequence is substituted with a sequence capable of undergoing specific DNA recombination by Cre recombinase in such a manner the functions of the proximal sequence element (hereinafter, referred to as "PSE") and the TATA box are not impaired, a method for producing the same and a method of using the same.

BACKGROUND ART

In eukaryotic organisms, there are commonly three types of RNA polymerases, that is, I to III. The polymerase III synthesizes low molecular weight RNA genes such as transfer RNA (hereinafter, referred to as "tRNA") and small nuclear RNAs (hereinafter, referred to as "snRNA". In the RNA synthesis by the polymerase III, the transcription start site is precisely determined, and the transcription is terminated by a sequence of five consecutive thymidines on DNA. In addition, at the end of the transcription, two or three adenyls are added. The polymerase III promoter includes two types of promoters, that is, a promoter with a TATA box, and a promoter without a TATA box. The polymerase III promoter with a TATA box is utilized for analysis of the gene function as described below.

In the post-genome sequence era, as a method for analyzing the gene function, an approach of reverse genetics such as RNA interference (hereinafter, referred to as "RNAi") by which determination of the base sequence of genes leads to identification of its function has gained attention. The RNAi is a phenomenon in which a double-stranded RNA (hereinafter, referred to as "dsRNA") constituted by a sense RNA that is homologous to a specific region of a gene whose function is desired to be inhibited and an anti-sense RNA interferes and destroys the homologous portion of mRNA that is a transcription product of the target gene.

For example, when a synthesized short chain interfering RNA (hereinafter, referred to as "siRNA") constituted by dsRNA of less than 30 base pairs is introduced into a mammal cell, mRNA having a homologous sequence is degraded. As a result, expression of proteins to which the target mRNA is to be translated is significantly reduced. Similarly, it has been made evident that RNAi can be induced by introducing a DNA vector expressing sense chain and anti-sense chain RNA simultaneously, or a hairpin RNA (hereinafter, referred to as "hpRNA") of invert repeat sequences, to a mammal cell. A method using the RNA polymerase III promoter at this time has been developed.

Nature Biotech (2002) 20: 446-448
Nature Biotech (2002) 19: 497-500

The RNA synthesis method employing RNA polymerase III promoters has made it possible to try to isolate a cell where RNAi is occurred constantly or to produce a transgenic (TG) mouse where RNAi is occurred for the purpose of analyzing the gene function.

Proc Natl Acad Sci USA. (2002) 99(8):5515-20
FEBS lett. (2002) 532 (1-2): 227-30

However, RNAi is a mechanism for suppressing gene expression, so that growth of a cell can be significantly affected, depending on the target gene whose expression is to be suppressed, and therefore it can be predicted that the cell where RNAi is occurred cannot be cloned or that a TG mouse that induces RNAi dies in the fetus stage. In order to prove a connection between suppressor genes and the abnormality of a phenotype more precisely, it is necessary to trigger RNAi in the development stage or only a specific tissue (organ) for analysis of the gene function.

In view of the above, it is expected to establish a method for inducing RNAi with the condition that RNAi can be induced in an arbitrary point of time, or only in a specific tissue (organ).

On the other hand, as a method for controlling so that a target gene becomes defective only under certain conditions or in a certain issue, a Cre-loxP system has been developed, and is used to produce, for example, knock-out mice or the like.

JP H1-112986A

This system utilizes the fact that Cre recombinase of a bacteriophage PI recognizes a loxP sequence of 34 bases, and DNA recombination is caused so that a loop-out occurs in a region between the loxP sequences, and this Cre-loxP system is known to function in mammal cells. In this system, when a configuration in which a stuffer flanked by the loxP sequences is arranged between a promoter and a target gene is used, in general, only the gene in the stuffer is expressed, and expression of the target gene is completely suppressed. However, Cre recombinase acts thereon, a homologous recombination occurs between the two loxP sequences. As a result, the stuffer gene is removed, and expression of the target gene is induced.

(Special issue of experimental medical science, The protocol series Experimental method for gene function inhibition, pp. 33 to 37, Tanabe, 2001)

Then, the inventors of the present invention tested to combine the RNAi method and the Cre-loxP system. However, when the target gene is a gene that is transcribed to a molecular inducing RNAi, in the Cre-loxP system in which a stuffer sequence flanked by loxP sequences is introduced between a promoter and a target gene, one of the loxP sequences remains, so that this is also transcribed together with the target gene and inserted in the RNAi molecule, so that the RNAi molecules results in having an inappropriate structure. As a result, the originally target RNAi failed to be occurred.

DISCLOSURE OF INVENTION

The inventors of the present invention found out that RNAi can occur without a loxP sequence being inserted in an RNAi molecule by transcription by substituting a part of an RNA polymerase III promoter with the loxP sequence in such a manner that a sequence necessary for transcription is not disturbed and thus achieved the present invention. The object thereof is to provide a novel RNA polymerase III promoter that can be used in a method for inducing RNAi with the condition that an RNAi molecule used for analysis of the gene function can be induced only in an arbitrary point of time or in a specific tissue (organ).

Another object of the present invention is to provide a novel RNA polymerase III promoter that can be used preferably for production of transgenic animals.

Hereinafter, the present invention will be described more specifically.

The above-described objects can be achieved by an RNA polymerase III promoter that is characterized in that a part of its sequence is substituted with a sequence capable of undergoing specific DNA recombination by Cre recombinase in such a manner the functions of PSE and a TATA box are not impaired.

The RNA polymerase III promoter of the present invention can be produced by substituting a part of its sequence with a sequence capable of undergoing specific DNA recombination by Cre recombinase in such a manner the functions of PSE and a TATA box are not impaired.

It is preferable that the sequence that is substituted with a sequence capable of undergoing specific DNA recombination by Cre recombinase is any of sequences between −50 and −1 from a transcription start site.

The sequence capable of undergoing specific DNA recombination by Cre recombinase used in the present invention is, for example, a loxP sequence or variants thereof.

The loxP sequence refers to a 34 bp sequence constituted by sequence-specific 13 base (ATAACTTCGTATA [SEQ ID NO. 9]) invert repeat sequences and a sequence-independent 8 base spacer sequence (FIG. 1(B)).

The variants thereof include a sequence in which the spacer sequence is substituted and the spacer sequence and a part of the invert repeat sequences are substituted, and a specific example is, for example, the sequence shown in disclosed in JP H11-196880A. It is preferable that the loxP sequence is substituted such that in the promoter after the substitution, a sequence from 10 to 25 of the loxP sequence is positioned so as to function as a TATA box.

The RNA polymerase III promoter used in the present invention is a sequence to which RNA polymerase III that synthesizes hpRNA or siRNA is bound at the start of transcription, and for example, a promoter for a H1 RNA gene or a promoter for a U6 RNA gene which have a transcription regulatory region upstream of a transcription start site can be used.

Any promoter that is derived from human or a mouse can be used as the RNA polymerase III promoter of the present invention.

Particularly preferable examples of the RNA polymerase III promoter of the present invention include the following RH-loxP promoter (RNAi-inducible H1 RNA gene promoter-loxP sequence fusion promoter).

Hereinafter, the present invention will be described more specifically by taking a RH-loxP promoter [SEQ ID NO. 1] as a specific example.

Production of RH-loxP Promoter

The RNA polymerase III promoter is suitable to synthesize a low molecular weight RNA gene such as tRNA or snRNA. It is known that the promoter III having a TATA box has fixed transcription start site and transcription termination site (see the section of Background Art).

For the RNAi induction that requires precise synthesis of RNA molecules, the transcription characteristics of the RNA polymerase III promoter are suitable to the synthesis of siRNA and hpRNA molecules.

Regarding an H1 RNA gene promoter, which is one of the RNA polymerase III promoter, its structure of the promoter has been significantly investigated, and it is shown that the octamer sequence (−97 to −90), the staf binding sequence (−88 to −69), the PSE sequence (−68 to −51), and the TATA box (−30 to −26) are important sequences for transcription (FIG. 1(A)).

In particular, the presence of the TATA box and PSE and their distance from the transcription start site are essential for transcription of the RNA polymerase III promoter. The loxP sequence is constituted by 34 base pairs of sequence-specific 13 base (ATAACTTCGTATA) [SEQ ID NO. 9]) invert repeat sequences and a sequence-independent 8 base spacer sequence, as described above (FIG. 1(B)).

Therefore, when this loxP sequence is substituted for −39 to −6 of the H1 promoter, the four sequences (octamer sequence, staf binding sequence, PSE sequence, TATA box sequence), which are necessary for transcription, are not disturbed, and the TATA box sequence (10 to 14) in the loxP sequence are substituted in the same positions as the TATA box sequence in the H1 promoter. Therefore, the RH-loxP promoter can be produced without impairing the function of the TATA box.

The loxP sequence will be further described.

Transformation and Position of loxP Sequence

As described above, the loxP sequence is a DNA sequence with 34 base pairs constituted by 13 base invert repeat structures and a 8 base spacer sequence, as described above. The spacer sequence can be more easily subjected to base substitution than the immobilized invert repeat structure. In the above-described example, when creating the RH-loxP promoter, the loxP sequence is substituted in the positions of −39 to −6 from the transcription start site of the H1 promoter without disturbing the TATA sequence (−30 to −26) of the H1 promoter, using the TATA sequence (10 to 14) in the loxP sequence. However, the substitution with the loxP sequence can be achieved without changing the distance of the TATA box sequence of the promoter from the transcription start site by transforming the spacer sequence or utilizing another TATA sequence (22 to 25) in the loxP sequence. Such a promoter can function in the same manner as the RH-loxP promoter.

The RNA polymerase III promoter of the present invention includes promoters in which a gene sequence is deleted, added, substituted or inserted in such a manner that the functions of a sequence capable of undergoing specific DNA recombination by Cre recombinase, PSE, and the TATA box are not impaired.

The RNA polymerase III promoter of the present invention can be used in the following manner.

(1) A structure is created in which in the downstream of the RNA polymerase III promoter including the loxP sequence of the present invention, a stuffer sequence, a fusion sequence of another loxP sequence and an RNAi-inducible sequence are arranged in this order. Such a structure transcribes only the sequence within the stuffer, and the RNA molecules that induce RNAi are not induced. However, when Cre recombinase (hereinafter, referred to as "Cre enzyme") is allowed to act thereon, the stuffer sequence is removed and the RNAi molecules can be induced.

(2) Furthermore, a target RNAi-inducible sequence is inserted downstream of the RNA polymerase III promoter including the loxP sequence of the present invention, and another loxP sequence is inserted further downstream. Such a structure inherently can induce RNAi, but when a Cre enzyme is reacted to remove the RNAi-inducible sequence flanked by the two loxP sequences, so that the RNAi can be cancelled.

(3) Furthermore, TG mice or cell strains can be produced by utilizing a system that can control expression of transcription products by the RNA polymerase III promoter including the loxP sequence of the present invention and another loxP sequence. The produced TG mice or cell strains can control expression of transcription products in a Cre enzyme dependent manner.

(4) Furthermore, the RNA polymerase III promoter including the loxP sequence of the present invention can induce expression of RNA genes. In other words, the RNA polymerase III promoter of the present invention can transcribe not only transcription products having an RNAi-inducible sequence, but also any other transcription products. In addition, by introducing a target transcription product gene between the RNA polymerase III promoter including the loxP sequence of the present invention and another loxP sequence, transcription can be induced and cancelled.

BRIEF DESCRIPTION OF DRAWINGS

FIG. 1 is a diagram showing the promoter sequence and the loxP sequence.
(A): human H1 RNA gene promoter [SEQ ID NO. 2]
(B): loxP sequence [SEQ ID NO. 3]
(C): RH-loxP promoter [SEQ ID NO. 4]

FIG. 3 is a view showing the results of cell observation in the fluorescence field when pcDNA3.1 plasmid, pUNO126, and pUNO137 were introduced respectively.

In FIG. 6, "ori" refers to a full-length plasmid before recombination with a Cre enzyme, and "recombinant" refers to a plasmid after recombination with a Cre enzyme.

FIG. 7 is a diagram showing DNA sequences in the vicinity of the transcription start site of the RH-loxP promoter of pUNO147 [SEQ ID NO. 5], pUNO149 [SEQ ID NO. 6], pUNO148 [SEQ ID NO. 7], and pUNO150 [SEQ ID NO. 8].

BEST MODE FOR CARRYING OUT THE INVENTION

Figure 2:
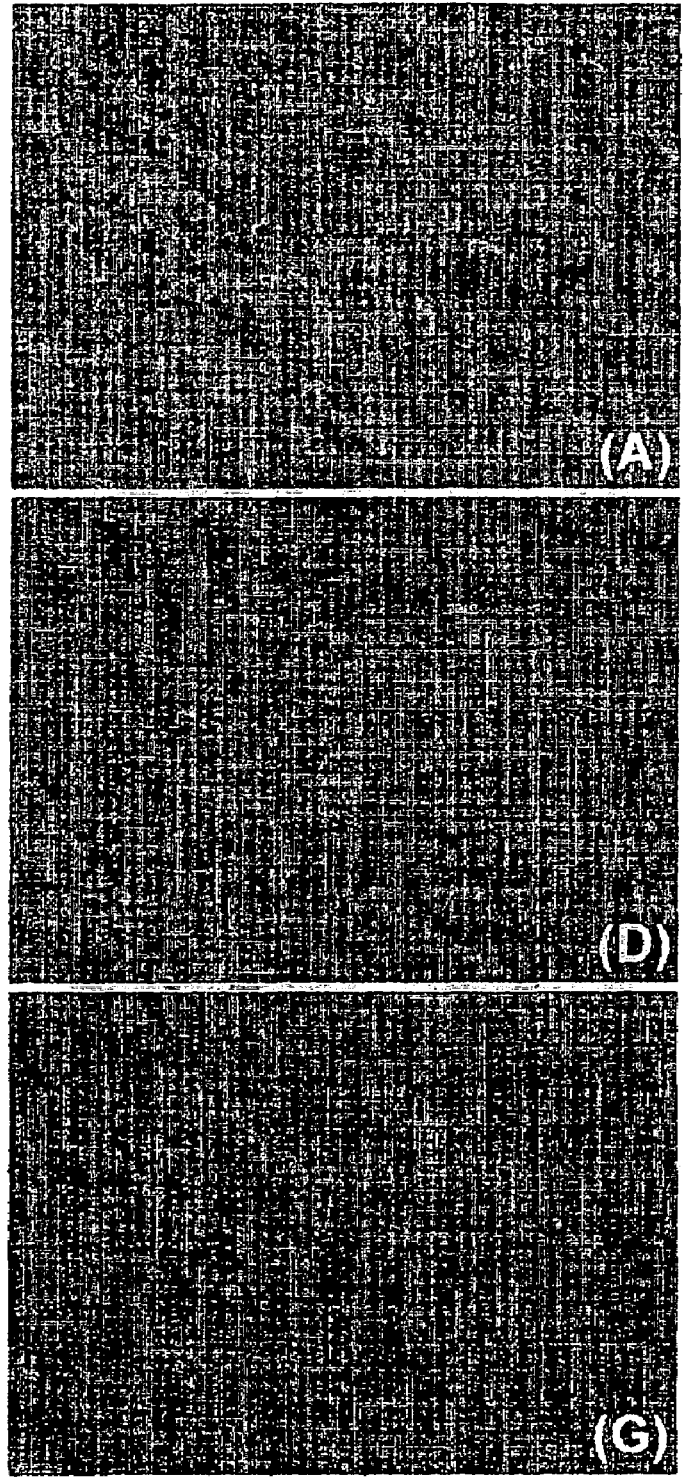
FIG. 2 is a view showing the results of cell observation in the bright field when pcDNA3.1 plasmid, pUNO126, and pUNO137 were introduced respectively.

Hereinafter, the present invention will be described more specifically by way of examples.

The cells and mice used in the present invention were obtained in the following manner.

HT1080/HB-EGF~YFP cells expressing a fusion protein of an HB-EGF gene and YFP (yellow fluorescent protein) were supplied by the Ehime University. EGFP (enhanced green fluorescent protein)-expressing transgenic mice (C57BL/6-TgN(ACTbEGFP)10sb; hereinafter, referred to as "eGFP mice") were purchased from Charles River Japan Inc.

EXAMPLE 1

(1) Production of Plasmid
(Production of Human H1 Promoter)

A human H1 promoter was amplified from human genomic DNA by PCR, using a primer (hH1/#3 5'-ggaattcttataggagagctgaagggaagg [SEQ ID NO. 10] hH1/#2 5'-gggatccgaagactatgggaaagagtggtctcatacag [SEQ ID NO. 11]. The amplified fragments were cleaved with restriction enzymes Eco RI and Bam HI, and cloned in Eco RI and Bam HI sites of pZErO I (Invitrogen Corp., Carlsbad, Calif., USA) (pUNO115).

(Production of Plasmid pUNO126)

In order to produce a plasmid pUNO126 that triggers RNAi to specifically inhibit HB-EGF gene expression dependently on a H1 promoter, PCR was performed, using a DNA primer (HB-EGF_KO2 5'-cagggcccaaaaaagctctttctggctgcagttctcttgaaactgcagccagaaagagctgggaaagagtggtctc [SEQ ID NO. 12] hH1/#5 5'-gctcgagttatagggagctgaagggaagg [SEQ ID NO. 13]) and pUNO115, and the amplified fragments were cloned in Eco RV site of pZErO I.

(Production of Plasmid pUNO137)

In order to produce a plasmid pUNO137 that triggers RNAi to specifically inhibit a HB-EGF gene expression dependently on a RH-loxP promoter, PCR was performed, using a DNA primer (HLX 5-gggatccaaaaaagctctttctggctgcagtttctcttgaaaactgcagcca-gaaagagctgggaaataacttcgtataacagaacttatacg aagttataatccaaagacatttcac [SEQ ID NO. 14] hH1/#4 5'-gactagtttatagggagctgaagggaagg [SEQ ID NO. 15]) and pUNO115, and the amplified fragments were cleaved with restriction enzymes Spe I and Bam HI, and cloned in Spe I and Bam HI sites of pZErO 2 (Invitrogen Corp., Carlsbad, Calif., USA).

(Production of Plasmid pUNO147)

A plasmid pUNO147 that triggers RNAi to specifically inhibit a HB-EGF gene expression dependently on a Cre enzyme was produced in the following manner.

First, using a DNA primer (L/H 5'-cctgcaggggaaataacttcgtataac:[SEQ ID NO. 16]hH1/#5 5'-gctcgagttatagggagctgaagggaagg [SEQ ID NO. 13]) and pUNO137, only the promoter site of pUNO137 was amplified by PCR and cloned in Eco RV site of pZErO I.

The base sequence was read, and clones in which the sequence of the L/H primer were adjacent to the Pst I site of pZErO I was isolated (pUNO142).

Furthermore, the loxP sequence of pUNO137 and an RNAi-inducible sequence with respect to the HE-EGF gene were amplified by PCR, using a DNA primer (L-Sp 5'-actagtcatgataacttcgtataagttctg [SEQ ID NO. 17], M13 r 5'-caggaaacagctatgac [SEQ ID NO. 18]) and pUNO137, cleaved with restriction enzymes Bam HI and Spe I, and cloned in Bam HI and Spe I sites of pZErO I (pUNO144).

Finally, pUNO147 was produced as follows. pUNO142 was cleaved with restriction enzymes Pst I and Pvu II, a sequence including a RH-loxP promoter was cloned in Pst I and Pvu II sites of pSV40/Zeo 2 (Invitrogen Corp., Carlsbad, Calif., USA) (pUNO143). Furthermore, a fragment including the loxP sequence obtained by cleaving pUNO144 with restriction enzymes Bam HI and Xba I was inserted in Nhe I and Bgl II sites of pUNO143.

(Production of Plasmid pUNO148)

A plasmid pUNO148 that triggers RNAi to specifically inhibit a YFP gene expression dependently on a Cre enzyme was produced in the following manner. DNA oligomer (EGLX_(AS)5'-cgagatctaaaaaacggccacaagt-tcagcgtgtctcttgaacacgctgaacttgtggccgtggg [SEQ ID NO. 19], EGLX_(S)5'-cgtcatgaataacttcgtataagttct-gttatacgaagttatttcccacggccacaagttcagc [SEQ ID NO. 20]) was synthesized, annealed and amplified by PCR, and the amplified fragments were cloned in a restriction enzyme site Eco RV of pZErO I. The base sequence was read, and clones in which the sequence of the EGLX_(AS) primer were adjacent to the Bam HI site of pZErO I were isolated (pUNO145).

A fragment including the loxP sequence obtained by cleaving pUNO145 with restriction enzymes Bam HI and Xba I was inserted in Nhe I and Bgl II sites of pUNO143.

(Production of Mouse U6 Promoter)

Mouse U6 promoters were amplified by PCR, using a mouse genomic DNA and a DNA primer (mU6/#1 5'-ggaat-tcatccgacgccgccatctcta [SEQ ID NO. 21], mU6/#2 5'-gggatc-cgaagaccacaaacaaggcttttctccaa [SEQ ID NO. 22]). The amplified fragments were cleaved with restriction enzymes Eco RI and Bam HI, and cloned in Eco RI and Bam HI sites of pZErO I (pUNO117).

(Production of Plasmid pUNO129)

In order to produce a plasmid pUNO129 that triggers RNAi to specifically inhibit a YFP gene expression dependently on a U6 promoter, PCR was performed, using a DNA primer (EGFP_KO1 5'-cggatccaaaaacggccacaagt-tcagcgtgtctcttgaacacgctgaacttgtggccgaaacaaggcttttctc [SEQ ID NO. 23], mU6/#1 5'-ggaattcatccgacgccgccatctcta [SEQ ID NO. 24]) and pUNO117, and the amplified fragments were cleaved with restriction enzymes Eco RI and Bam HI, and cloned in Eco RI and Bam HI sites of pZErO I.

(2) Transfection

A HT1080/HB-EGF-YFP cell expresses a fusion protein of an HB-EGF gene and a YFP gene. Various plasmids were subjected to gene introduction to HT1080/HB-EGF-YFP cells, using Lipofectamine 2000 (Invitrogen Corp., Carlsbad, Calif., USA).

Lipofectamine 2000 (3.0 microliters) was diluted with 100 microliters of Opti-MEM (Gibco) and was allowed to stand at room temperature for 5 min. DNA (1.6 micrograms) was diluted with 100 microliters of Opti-MEM. These solutions were mixed and allowed to stand at room temperature for 20 min. Then, the mixed solution was added with 1 ml of Opti-MEM to 12 well plate cells. Four hours later, the DNA/Lipofectamine mixed solution was removed and substituted with a culture solution.

(3) Cre-loxP Recombination Reaction:

A Cre recombination reaction of pUNO147 or pUNO148 was performed with Cre recombinase purchased from Clontech Laboratories, Inc. 200 ng of plasmid was reacted in 20 microliters of a reaction solution including 1 microliter of Cre enzymes, 2 microliters of 10× buffer, and 2 microliters of BSA (1 mg/ml) for 15 min at room temperature. After the reaction, the plasmid was incubated at 70° C. for 5 min in order to deactivate the enzymes.

(4) Gene Introduction to Mouse:

100 micrograms of plasmid DNA were diluted with 3 ml of Ringer's solution (147 mM NaCl, 4 mM KCl, 1.13 mM $CaCl_2$). Tail intravenous injection was performed through a 27-gauge needle for 7 seconds.

The following is illustrative results of tests performed using the RH-loxP promoter.

(1) RNAi Induction by RH-loxP Promoter:

In order to confirm whether or not the designed RH-loxP promoter induces RNAi, an RNAi-inducible sequence (hpRNA) with respect to human HB-EGF was inserted downstream of the RH-loxP promoter or H1 promoter. pUNO126 that was designed to transcribe hpRNA from the H1 promoter, pUNO137 that was designed to transcribe hpRNA from the RH-loxP promoter, and pcDNA3.1 plasmid as a control were each introduced in HT1080/HB-EGF~YFP that expresses HB-EGF-YFP fusion protein.

Then, 48 hours later, the effect of suppressing expression of the HB-EGF gene was confirmed by observation of emission of the YFP protein with a fluorescence microscope.

FIG. 2 shows the results of cell observation in the bright field when pcDNA3.1 plasmid, pUNO126, and pUNO137 were each introduced.

FIG. 3 shows the results of cell observation in the fluorescence field when pcDNA3.1 plasmid, pUNO126, and pUNO137 were each introduced.

The presence of the HB-EGF~YFP fusion protein was observed with green emission.

Figure 4:
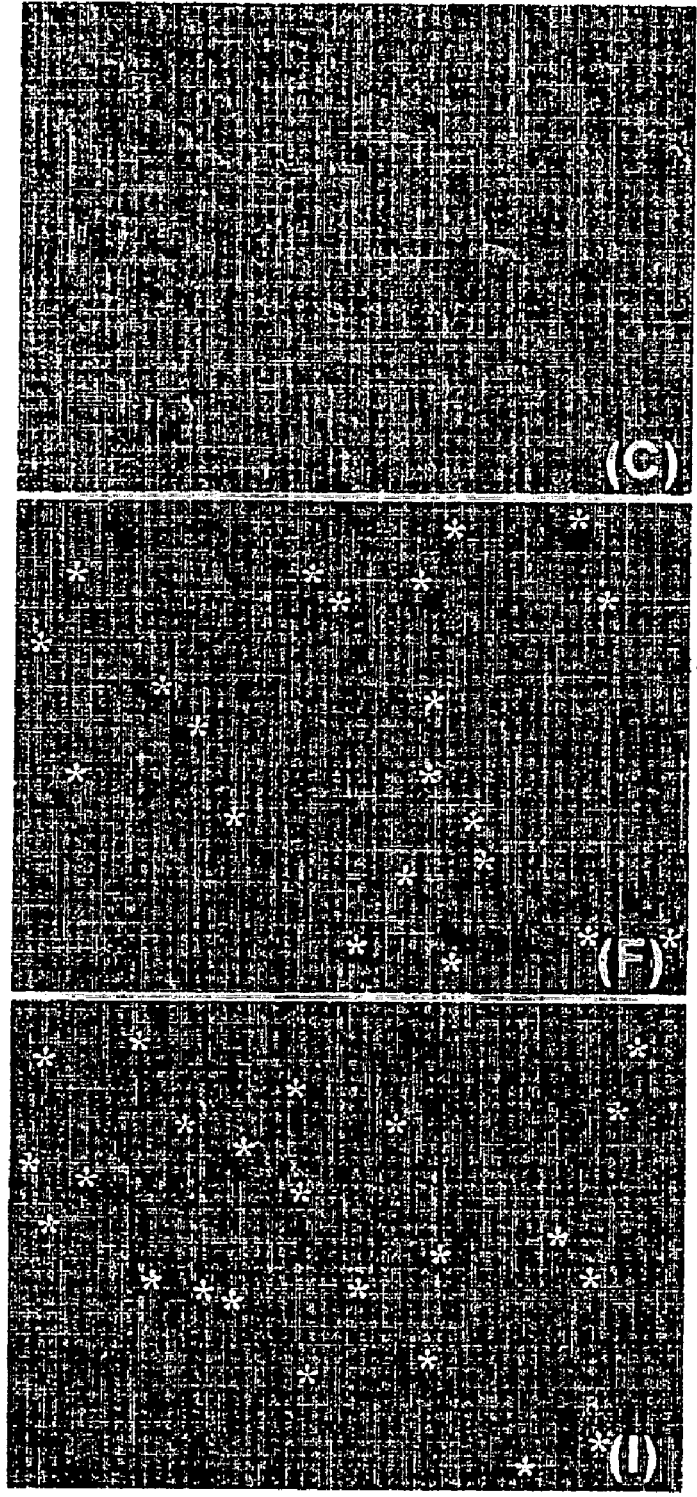
FIG. 4 is a view obtained by superposing FIGS. 2 and 3. An asterisk (*) marks a cell that does not exhibit fluorescence.

FIG. 4 is a view obtained by superposing FIGS. 2 and 3.

In (C), it was confirmed that almost all cells express the HB-EGF~YFP protein.

In (F), green emission, which is derived from HT1080/HB-EGF~YFP, was not confirmed in the cells shown by an asterisk (*).

In (I) as well, there were some cells that did not exhibit green emission, which is derived from HB-EGF~YFP, as shown by an asterisk (*).

This means that pUNO126 suppresses HB-EGF gene expression. Thus, it was confirmed that hpRNA that is transcribed from the H1 promoter triggers RNAi.

The gene introduction of plasmid pUNO150 that was designed to transcribe an hpRNA molecule with respect to the YFP gene from the RH-loxP promoter to a HT1080/HB-EGF~YFP cell, as well as the gene introduction of plasmid pUNO129 that was designed to transcribe an hpRNA molecule with respect to the YFP gene from the mouse U6 RNA gene promoter to a HT1080/HB-EGF~YFP cell, reduced the amount of HB-EGF~YFP present and showed the RNAi effect.

The RNAi effect of a target gene product was provided by the gene introduction of plasmids (pUNO137 and pUNO150) that were designed to transcribe an hpRNA molecule dependently on the RH-loxP promoter to HT1080/HB-EGF~YFP cells, which indicates that the RH-loxP promoter effectively serves to induce RNAi and is appropriate for transcription synthesis of hp RNA molecules, as well as the RNA polymerase III promoter (H1 promoter and U6 promoter).

(2) Recombination Reaction of RH-loxP Promoter with Cre Enzyme

Figure 5:
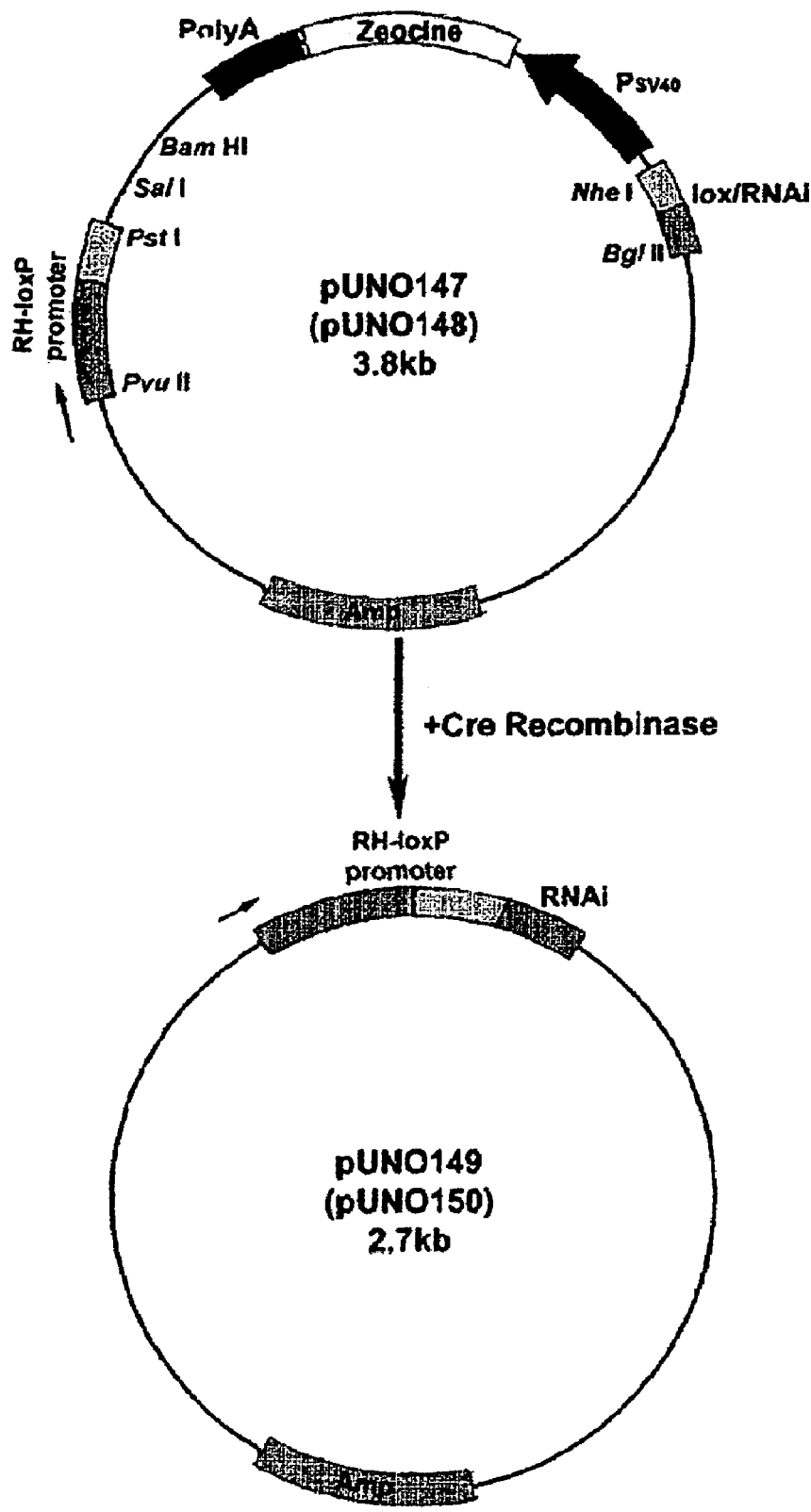
FIG. 5 is an outline of a reaction of the RH-loxP promoter caused by Cre enzymes.

In order to confirm whether or not the designed RH-loxP promoter performs a loxP sequence-specific recombination reaction with Cre enzymes, pUNO147 and pUNO148 plasmids were produced.

pUNO147 was produced by inserting the RH-loxP promoter in the direction from the restriction enzyme site Pvu II to the restriction enzyme site Pst I of SV40/Zeo2, and furthermore inserting a fusion sequence of a sequence (loxP sequence+ttccc) that matches −39 to −1 of the RH-loxP promoter sequence and an hpRNA sequence with respect to the HB-EGF gene in the direction from the restriction enzyme site Nhe I to the restriction enzyme site Bgl II (FIG. 5).

pUNO148 was produced by inserting hpRNA with respect to the YFP gene, instead of hpRNA with respect to the HB-EGF gene of pUNO 147.

pUNO147 and pUNO148 were reacted with Cre enzymes. After the reaction, in order to reduce unreacted plasmid, a reaction was performed with restriction enzymes Sal I and Bam HI, and then the plasmid was transformed into *E. coli*, and thus a single clone was obtained.

The obtained clone was spread in an ampicillin medium and a zeocine medium with a toothpick to perform screening.

pUNO147 and pUNO148 have an ampicillin resistant gene and a zeocine resistant gene, and their clones are resistant to both of the antibiotics. However, the recombinant has only an ampicillin resistant gene, and is not grown in a zeocine medium.

As a result of screening, 83% of the clones are resistant to ampicillin and sensitive to zeocine. Therefore, such clones are expected to be recombinants that have lost the zeocine resistant gene as shown by pUNO149 and pUNO150 (FIG. 5).

Plasmids were extracted and analyzed in order to confirm whether the clones having lost the zeocine resistance are results of the fact that a recombinant reaction occurred specifically to the loxP sequence, and that a region (1.1 kbp) between the loxP sequences including the zeocine resistant gene was looped out.

Figure 6:
FIG. 6 is a view showing electrophoresis of a recombinant (pUNO149 and pUNO150) generated by a Cre enzyme of pUNO147 and pUNO148.

FIG. 6 shows results of extracting plasmids from the clones that have lost the zeocine resistance as a result of the recombinant reaction and analyzing it. The length of the plasmids of the clones that have lost the zeocine resistance is shorter than that of the plasmids before the recombinant reaction. This is expected to be a result of the fact that a region between the loxP sequences was looped out with Cre enzymes.

Finally, the DNA sequence of the recombinant obtained by the Cre reaction was investigated (FIG. 7). In the sequence before the Cre enzyme reaction, a sequence that is derived from pSV40/Zeo2 was seen at the transcription start site. However, in the sequence after the Cre enzyme reaction, an RNAi-inducible sequence has been newly inserted at the transcription start site. Furthermore, the DNA sequence of the region including the zeocine resistant gene between the loxP sequences was not seen. Therefore, it can be said that the region between the loxP sequences including the zeocine resistant gene was looped out dependently on the Cre enzyme, and an RNAi-inducible sequence was disposed at the transcription start site.

These results show that the RH-loxP promoter can cause a loxP sequence-specific recombination reaction with Cre enzymes.

(3) RNAi Induction by Cre-loxP Recombination Reaction

In order to confirm that pUNO148 causes a recombination reaction in a cell dependently on Cre enzymes, and induces RNAi, pUNO148 and pMC-Cre plasmid expressing Cre enzymes were simultaneously introduced to HT1080/HB-EGF~YFP cells, and 48 hours later, emission of YFP was observed with a fluorescence microscope, and thus the RNAi effect was confirmed.

Figure 8:
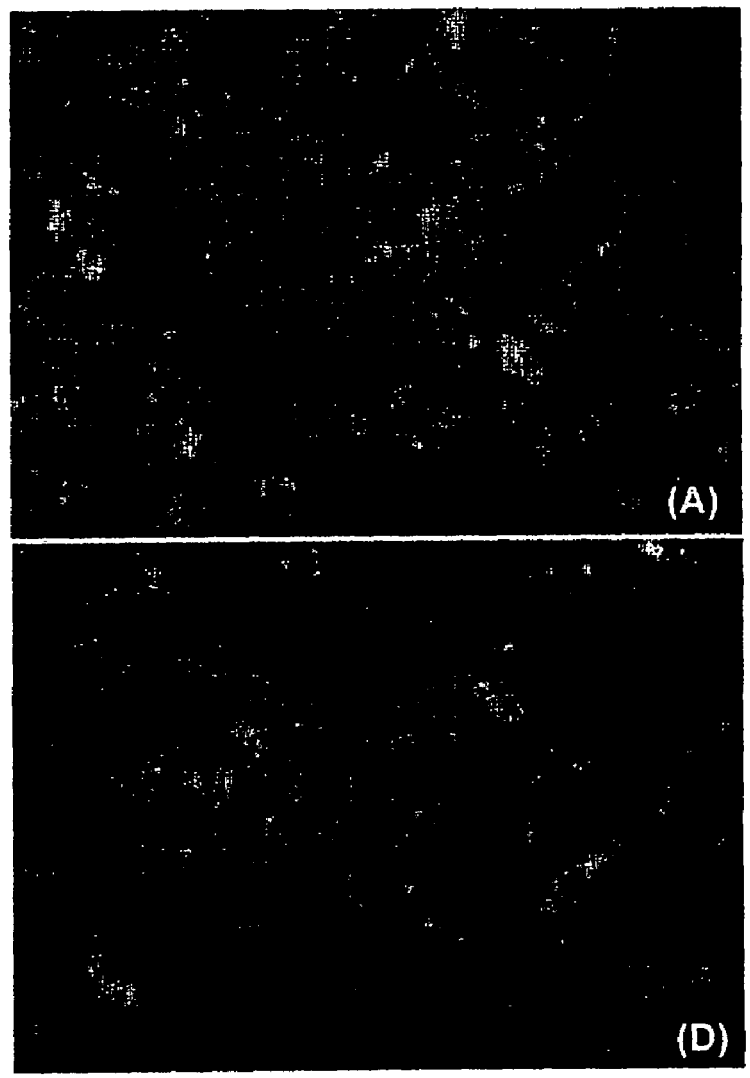
FIG. 8 is a view showing the results of cell observation in the fluorescence field when only pUNO148 was introduced or pUNO148 and pMC-Cre plasmid were simultaneously introduced.

FIG. 8 shows the results of cell observation in the fluorescence field when only pUNO148 was introduced or pUNO148 and pMC-Cre plasmid were simultaneously introduced.

Figure 9:
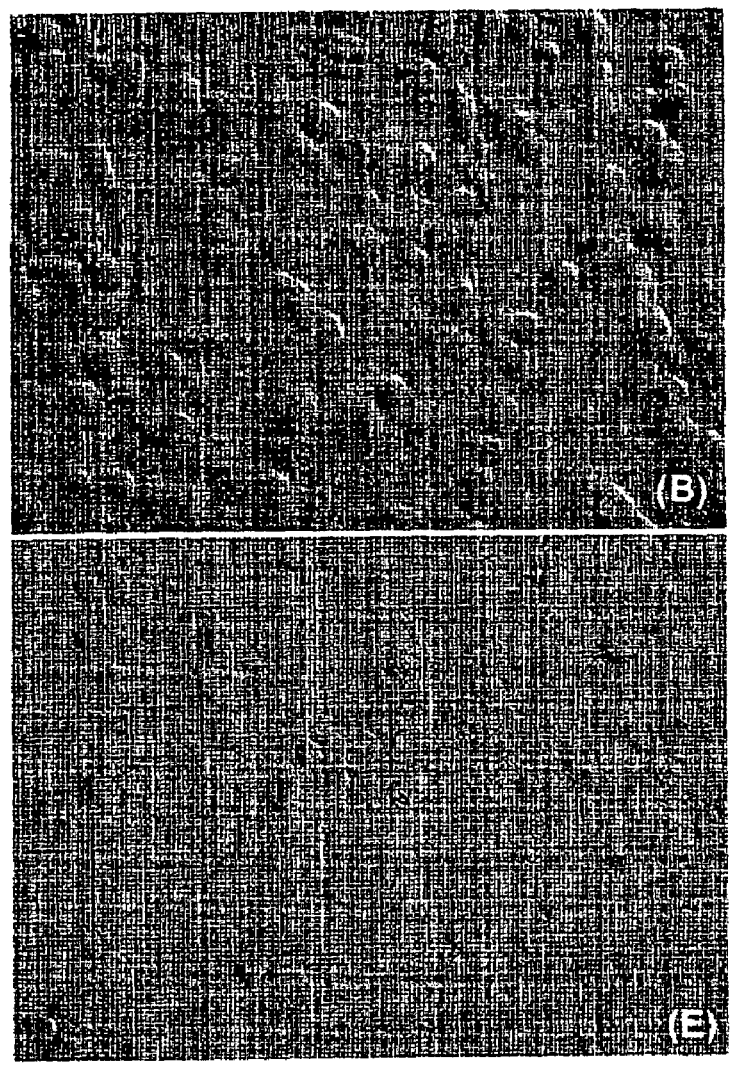
FIG. 9 is a view showing the results of cell observation in the bright field when only pUNO148 was introduced or pUNO148 and pMC-Cre plasmid were simultaneously introduced.

FIG. 9 shows the results of cell observation in the bright field when only pUNO148 was introduced or pUNO148 and pMC-Cre plasmid were simultaneously introduced.

Figure 10:
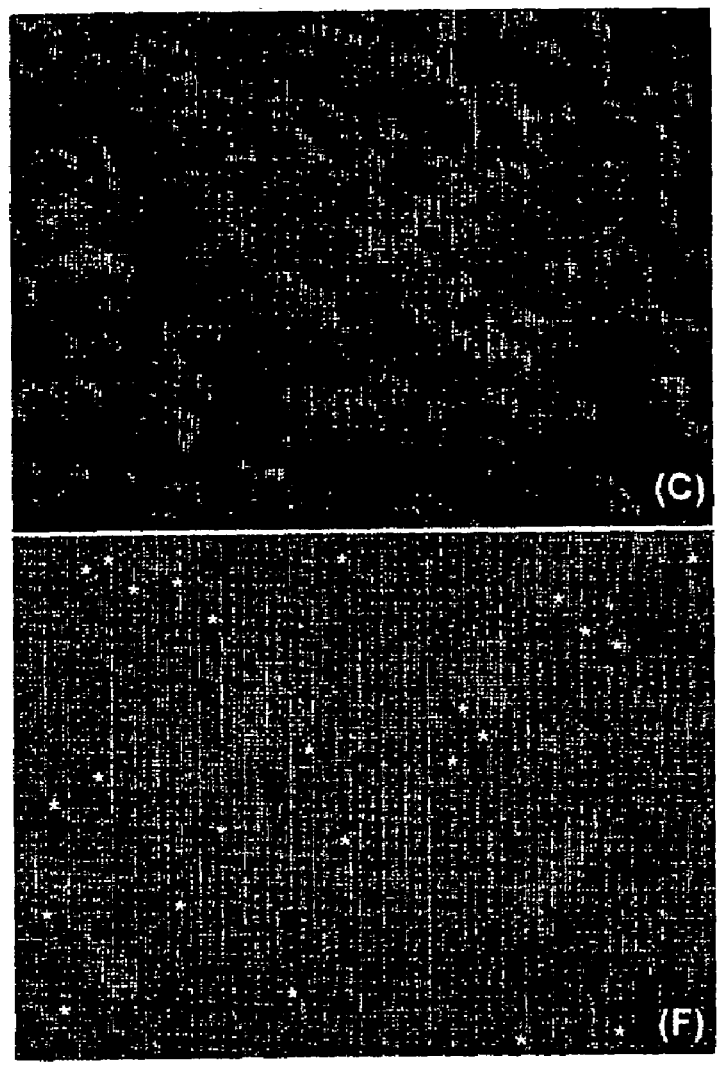
FIG. 10 is a view obtained by superposing FIGS. 8 and 9. An asterisk (*) marks a cell that does not exhibit fluorescence.

FIG. 10 is a view obtained by superposing FIGS. 8 and 9.

Since almost all cells to which pUNO148 had been introduced exhibited fluorescence, the YFP protein was present in almost all the cells. On the other hand, in the cells to which pUNO148 and pMC-Cre plasmid had been simultaneously introduced, fluorescence was observed in 80% of the cells that were confirmed in the bright field, but fluorescence was not observed in 20% thereof (FIG. 8(D), FIG. 9(E) and FIG. 10(F)).

The number of the cells that have lost fluorescence due to plasmid introduction of the cells to which pUNO148 and pMC-Cre had been simultaneously introduced was clearly larger than that of the cells to which pUNO148 had been introduced.

This result shows that the RNAi effect was not provided in the pUNO148-introduced cells, but the RNAi effect was provided in the cells to which pUNO148 and pMC-Cre have been simultaneously introduced.

Therefore, the results show that in the cells to which pUNO148 and pMC-Cre enzyme have been simultaneously introduced, a Cre-loxP recombination reaction as shown in FIG. 5 was caused by the Cre enzyme that is expressed by the pMC-Cre, and the pUNO148 was changed into an RNAi induction recombinant.

(4) RNAi Effect in Living Mice:

As described above, in cells, the RNAi effect was induced by the Cre enzyme from pUNO148.

Next, it was investigated whether the same could be observed in living mice. 3 ml of Ringer's solution including 100 micrograms of plasmids were injected through the veins of the tails of transgenic mice expressing EGFP gene (EGFP TG; hereinafter, referred to as "eGFP"), and 72 hours later, the livers were irradiated with UV rays, and then the presence of EGFP protein was observed.

Furthermore, the livers were extracted and the quantity of the EGFP protein was determined in the following method.

Each liver was homogenized in a PBS solution, and centrifuged at 1000 rpm, and the supernatant was separated as an extract. The concentration of the protein in the extract obtained from each liver was measured and adjusted to the same. The fluorescence intensity of EGFP contained in the extract was measured using POLARstar (Biotechnology & Life Sciences). The data was expressed as a relative value of the fluorescence intensity of each sample, taking the fluorescence intensity of a sample from a liver of an eGFP mouse to which only Ringer's solution was injected as 100.

Figure 11:
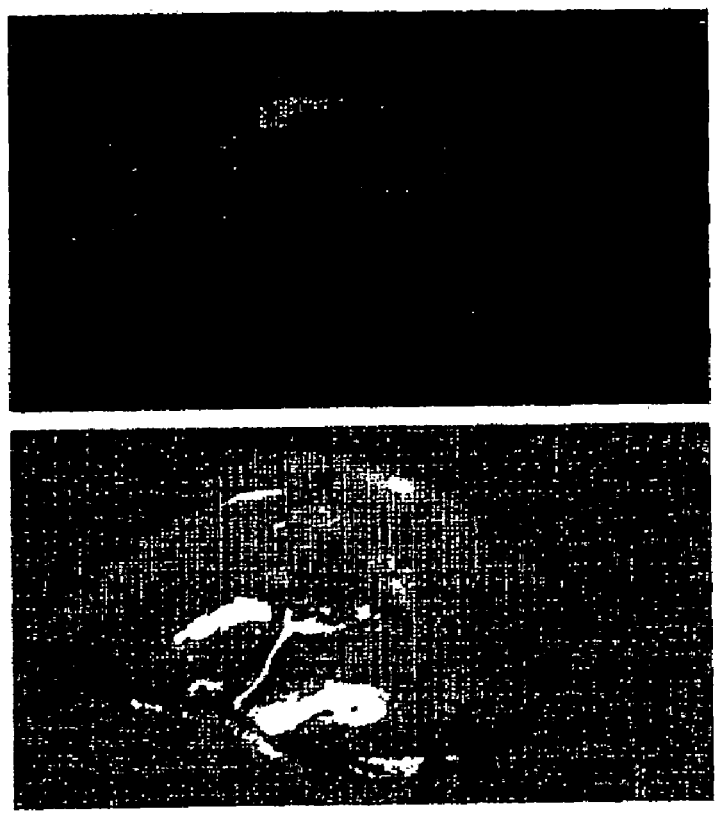
FIG. 11 is a view showing the liver of a C57BL mouse (WT mouse) to which only a Ringer's solution is injected.

For control, in an eGFP mouse to which only the Ringer's solution had been injected, the presence of EGFP was more prominent (FIG. 12) than in the liver of a C57BL (wild type; hereinafter, referred to as "WT") mouse to which only the Ringer's solution had been injected (FIG. 11).

Figure 13:
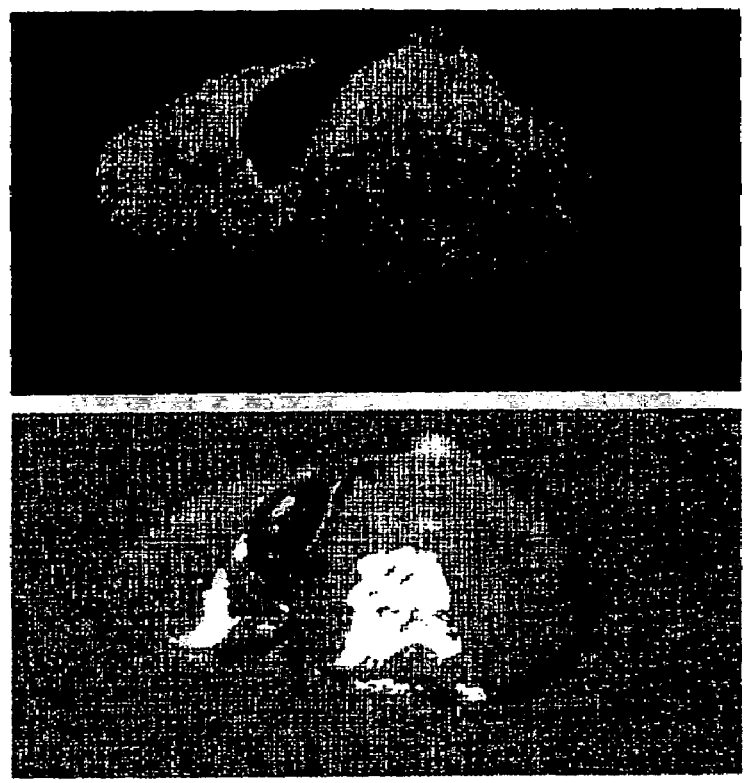
FIG. 13 is a view showing the liver of an eGFP mouse to which 100 micrograms of pUNO129 was injected.

Next, the pUNO129 plasmid is a plasmid that induces the RNAi to specifically inhibit the YFP gene expression, as described above, and the sequence that is recognized in the induction is also present in a transcription product of the EGFP gene. Therefore, when the pUNO129 plasmid was injected to an eGFP mouse, a reduction of expression of EGFP was observed in the liver (intermediate lobe) (FIG. 13).

Figure 15:
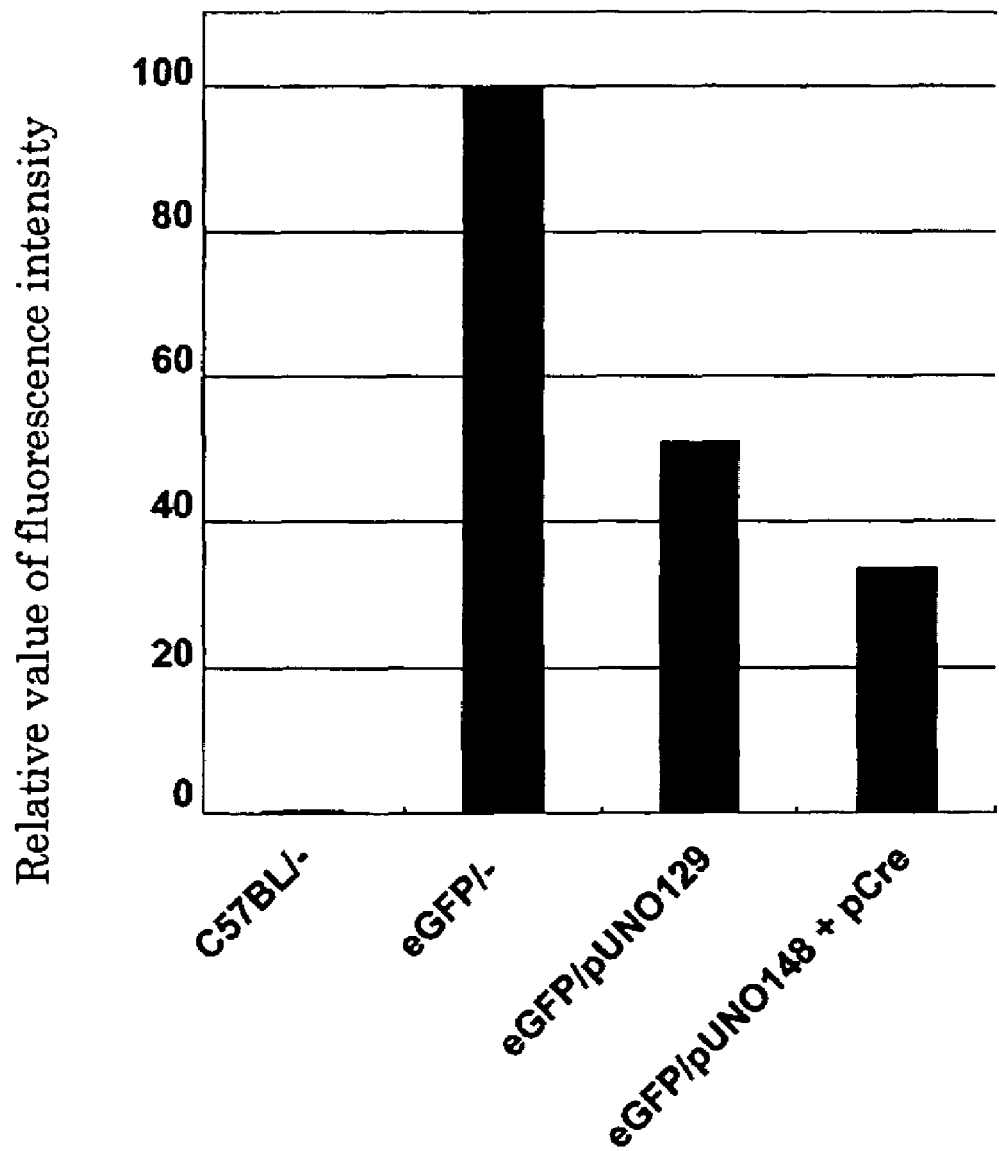
FIG. 15 is a graph showing the EGFP expression amount in a living mouse with respect to FIGS. 11 to 14 as relative values, taking the fluorescence intensity when only a Ringer's solution was injected as 100.

Furthermore, when the EGFP amount was determined, the EGFP amount in the liver of the eGFP mouse to which pUNO129 had been injected was 49% smaller than the EGFP amount of the liver of the eGFP mouse to which only the Ringer's solution had been injected (FIG. 15).

Similarly, pUNO148 is a plasmid that induces the RNAi to specifically inhibit the YFP gene expression when it is used together with pMC-Cre plasmid, as described above, and the sequence that is recognized in the induction is also present in a transcription product of the EGFP gene. Therefore, pUNO148 and pMC-Cre plasmids were simultaneously injected to eGFP mice. In the liver in this case, emission derived from the EGFP protein was lost so as to form dots (FIG. 14), and the EGFP amount was reduced by 67% (FIG. 15).

These results are believed to show that, similarly to the results of the fact that in the HT1080/HB-EGF~YFP cultured cells, pUNO148 was recombined into an RNAi-inducible plasmid by the Cre enzyme (FIGS. 8 to 10), the Cre enzyme that had been expressed in the mouse liver recombined the pUNO148 plasmid into an RNAi-inducible plasmid, so that expression of the EGFP gene was suppressed.

These results show that the RH-loxP promoter including the loxP sequence can induce the RNAi effect dependently on the Cre enzyme also in living mice.

Hereinafter, the drawings will be described.

(FIG. 1: Promoter Sequence and loxP Sequence)

(A) Human H1 RNA Gene Promoter

The sequence from −97 to −90 shows an octamer sequence, the sequence from −88 to −69 shows a staf binding region, the sequence from −68 to −51 shows a PSE sequence, a sequence from −30 to −26 shows TATA-box, and +1 shows a transcription start site. The numbers show the number of bases from the transcription start site.

(B) loxP Sequence

The loxP sequence has an invert repeat structures of 13 bases corresponding to 1 to 13 and 22 to 34. The underlined sequence is a variable 8 base spacer sequence in the loxP sequence. The number shows the number of bases.

(C) RH-loxP Promoter

The RH-loxP promoter was obtained by modifying a H1 RNA gene promoter as the basis. A sequence from −39 to −6 of the H1 promoter was substituted with the loxP sequence shown in (B). The loxP sequence is shown by upper case letters, and the underlined sequence matches the variable spacer in the loxP sequence. The octamer sequence (−97 to −90), the staf binding region (−88 to −69), the PSE sequence (−68 to −51), the TATA-box (−30 to −26), and the transcription start site at +1 are the same as those in (A). (In the sequence of FIG. 1(C), the upper case letters show the loxP sequence. The underlined sequence shows the variable spacer in the loxP sequence. +1 shows the transcription start site.)

(FIGS. 2 to 4: Suppression of HB-EGF Gene Expression by hpRNA Synthesized from the RH-loxP Promoter)

pcDNA3.1 plasmid (FIGS. 2(A), 3(B), and 4(C)), a plasmid pUNO126 with which an RNAi-inducible sequence hpRNA with respect to the HB-EGF gene had been synthesized from the H1 promoter (FIGS. 2(D), 3(E), and 4(F)), or a plasmid pUNO137 with which an RNAi-inducible sequence hpRNA with respect to the HB-EGF gene is expressed from the RH-loxP promoter (FIGS. 2(G), 3(H), and 4(I)) was each subjected to gene introduction to an HT1080/HB-EGF~YFP cell constantly expressing a fusion protein of the HB-EGF gene and the YFP gene, and were observed in the bright field (FIG. 2) and the fluorescence field (FIG. 3) 48 hours later. FIG. 4 is obtained by superposing FIGS. 2 and 3, and cells that do not exhibit fluorescence are shown by an asterisk (*) therein.

(FIGS. 5 to 7: Reaction of RH-loxP Promoter with Cre Enzyme)

FIG. 5: the Outline of a Reaction of RH-loxP Promoter with Cre Enzyme pUNO147 has the RH-loxP promoter, the stuffer sequence (a sequence with 1.1 kbp including the zeocine resistant gene), and a fusion sequence of a sequence (loxP sequence+ttccc) that matches −39 to −1 of the RH-loxP promoter and an hpRNA synthesis sequence with respect to the HB-EGF gene.

pUNO148 has the RH-loxP promoter, the stuffer sequence (a sequence with 1.1 kbp including the zeocine resistant gene), and a fusion sequence of a sequence (loxP sequence+ttccc) that matches −39 to −1 of the RH-loxP promoter and an hpRNA synthesis sequence with respect to the YFP (or EGFP) gene.

pUNO147 and pUNO148 do not have the hpRNA synthesis sequence at the transcription start site of the RH-loxP promoter.

pUNO147 and pUNO148 are changed into pUNO149 and pUNO150, respectively, in which by a Cre enzyme reaction, the stuffer sequence is looped out and the hpRNA synthesis sequence is present at the transcription start site of the RH-loxP promoter.

pUNO147 and pUNO148 have resistant genes to both antibiotics ampicillin and zeocine, but pUNO149 and pUNO150 only have an ampicillin resistant gene. In FIG. 5, restriction enzyme sites Pvu II, Pst I, Sal I, Bam HI, Nhe I and Bgl II are shown. The arrows in FIG. 5 indicate the direction of transcription of the RH-loxP promoter.

FIG. 6: Electrophoretogram of Recombinants (pUNO149 and pUNO150) Produced by Cre Enzyme of pUNO147 and pUNO148 pUNO147 and pUNO148 were each reacted with Cre enzymes in a test tube. After reaction using restriction enzymes Sal I and Bam HI, the plasmids were transformed into E. coli so that clones were obtained. By screening, clones that are resistant to antibiotic ampicillin and sensitive to antibiotic zeocine were obtained, and plasmids were extracted from respective clones and then subjected to electrophoresis analysis using 0.8% agarose gel.

Lane 1 shows pUNO147 that has not been reacted with Cre enzymes, lane 2 shows a recombinant pUNO149 that was obtained by reacting pUNO147 with Cre enzymes, and lane 3 shows a recombinant pUNO150 that was obtained by reacting pUNO148 with Cre enzymes.

FIG. 7: DNA Sequence in the Vicinity of Transcription Start Site of the RH-loxP Promoter of pUNO147, pUNO149, pUNO148, and pUNO150

The DNA sequence was analyzed using a DNA primer (M13 (−20) Forward primer; 5'-gtaaaacgacggccagt [SEQ ID NO. 25]). The transcription start site is shown by +1. A portion enclosed by a square shows a homologous sequence in the hpRNA, and the underlined portion shows a loop structure in the hpRNA, and the double underlined portion shows a transcription termination sequence.

(FIGS. 8 to 10: Suppression of HB-EGF~YFP Gene Expression by hpRNA that is Induced by Cre Enzymes)

pUNO148(A to C), or pUNO148 and pMC-Cre (Cell, 1993, 73, 1155-1164) (D to F) were subjected to gene introduction to HT1080/HB-EGF~YFP cells constantly expressing a fusion protein of the HB-EGF gene and the YFP gene, and was observed in the fluorescent field (A, D) or the bright field (B, E) 48 hours later. (C, F) are views obtained by superposing the views in the same field observed in the bright field and the fluorescent field in which cells that do not exhibit fluorescence are shown by an asterisk (*).

(FIGS. 11 to 14: Suppression of EGFP Gene Expression by hpRNA Expression that is Induced by Cre Enzymes in Living Mice)

A plasmid that was adjusted with a Ringer's solution was injected through the veins of the tail of mice, and the livers were observed 72 hours later.

FIG. 11 shows the liver of a C57BL mouse (WT mouse) to which only Ringer's solution was injected.

Figure 12:
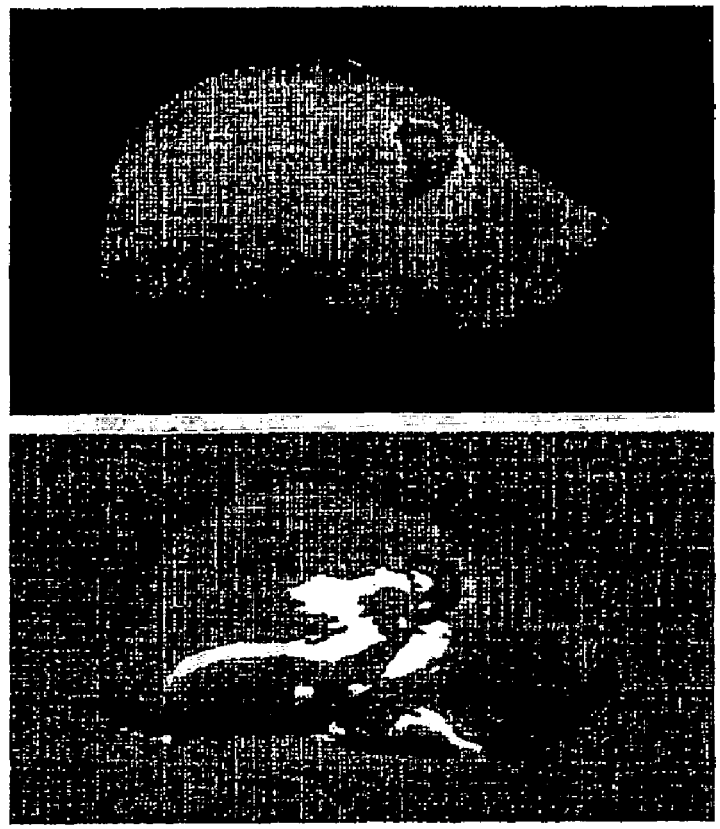
FIG. 12 is a view showing the liver of a transgenic mouse (eGFP mouse) constantly expressing EGFP protein, to which a Ringer's solution was injected.

FIG. 12 shows the liver of a transgenic mouse (eGFP mouse) constantly expressing EGFP protein to which Ringer's solution was injected.

FIG. 13 shows the liver of an eGFP mouse to which 100 micrograms of pUNO129 was injected.

Figure 14:
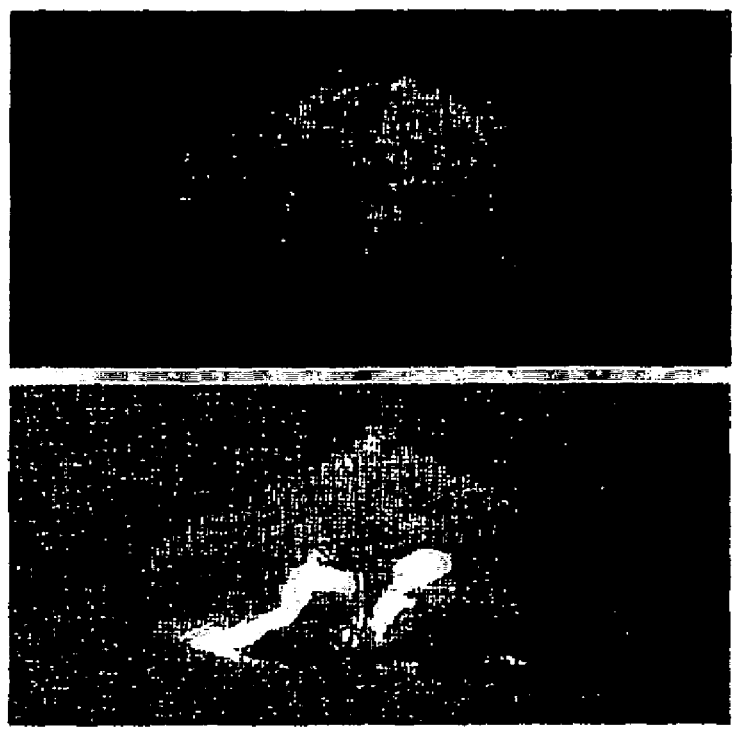
FIG. 14 is a view showing the liver of an eGFP mouse to which pMC-Cre plasmid (80 micrograms) and pUNO148 (20 micrograms) were injected.

FIG. 14 shows the liver of an eGFP mouse to which pMC-Cre plasmid (80 micrograms) and pUNO148 (20 micrograms) were injected. The lower view results from observation in the bright field, and the upper view results from observation with irradiation of a UV lamp.

INDUSTRIAL APPLICABILITY

By using the RNA polymerase III promoter of the present invention, RNAi can be induced or cancelled as appropriate. Furthermore, by using the RNA polymerase III promoter of the present invention, TG mice or cell strains can be produced as appropriate, and the produced TG mice or cell strains can control synthesis of transcription products dependently on Cre enzymes. Furthermore, by using the RNA polymerase III promoter of the present invention, expression of RNA genes can be induced as appropriate.

```
                              SEQUENCE LISTING

<160> NUMBER OF SEQ ID NOS: 1

<210> SEQ ID NO 1
<211> LENGTH: 100
<212> TYPE: DNA
<213> ORGANISM: Artificial Sequence
<220> FEATURE:
<221> NAME/KEY: promoter
<223> OTHER INFORMATION: Chemically synthesized

<400> SEQUENCE: 1
aatatttgca tgtcgctatg tgttctggga aatcaccata aacgtgaaat            50
gtctttggat tataacttcg tataatgtat ggtatacgaa gttatttccc           100
```

The invention claimed is:

1. An RH (RNAi-inducible H1)-loxP promoter comprising SEQ ID NO: 1.

* * * * *

UNITED STATES PATENT AND TRADEMARK OFFICE
CERTIFICATE OF CORRECTION

PATENT NO. : 7,504,492 B2  Page 1 of 11
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

In columns 13 and 14, after "SEQUENCE LISTING", change

```
"  <160>  NUMBER OF SEQ ID NOS: 1

<210>  SEQ ID NO  1
   <211>  LENGTH:  100
   <212>  TYPE:  DNA
   <213>  ORGANISM:  Artificial Sequence
   <220>  FEATURE:
   <221>  NAME/KEY:  Promoter
   <223>  OTHER INFORMATION:  Chemically synthesized <400>  SEQUENCE:  1
   aatatttgca tgtcgctatg tgttctggga aatcaccata aacgtgaaat        50
gtctttggat tataacttcg tataatgtat ggtatacgaa gttatttccc       100 "
``` to be

```
-- <160>  NUMBER OF SEQ ID NOS: 25
```

UNITED STATES PATENT AND TRADEMARK OFFICE
CERTIFICATE OF CORRECTION

PATENT NO. : 7,504,492 B2
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

```
<210>  SEQ ID NO  1
<211>  LENGTH:  100
<212>  TYPE:  DNA
<213>  ORGANISM:  Artificial <220>  FEATURE:
<221>  NAME/KEY:  Promoter
<223>  OTHER INFORMATION:  Chemically synthesized <400>  SEQUENCE:  1
aatatttgca tgtcgctatg tgttctggga aatcaccata aacgtgaaat gtctttggat    60
tataacttcg tataatgtat ggtatacgaa gttatttccc                         100

<210>  SEQ ID NO  2
<211>  LENGTH:  101
<212>  TYPE:  DNA
<213>  ORGANISM:  Homo sapiens <400>  SEQUENCE:  2
aatatttgca tgtcgctatg tgttctggga aatcaccata aacgtgaaat gtctttggat    60
ttgggaatct tataagttct gtatgagacc actctttccc a                       101

<210>  SEQ ID NO  3
<211>  LENGTH:  34
<212>  TYPE:  DNA
<213>  ORGANISM:  Bacteriophage P1

<400>  SEQUENCE:  3
ataacttcgt ataatgtatg gtatacgaag ttat                                34
```

UNITED STATES PATENT AND TRADEMARK OFFICE
CERTIFICATE OF CORRECTION

PATENT NO.       : 7,504,492 B2
APPLICATION NO.  : 10/545946
DATED            : March 17, 2009
INVENTOR(S)      : Hiroyuki Ueno et al.

It is certified that error appears in the above-identified patent and that said Letters Patent is hereby corrected as shown below:

```
<210>  SEQ ID NO  4
<211>  LENGTH: 101
<212>  TYPE: DNA
<213>  ORGANISM: Artificial <220>  FEATURE:
<223>  OTHER INFORMATION: RH-loxP promoter sequence <400>  SEQUENCE: 4
aatatttgca tgtcgctatg tgttctggga aatcaccata aacgtgaaat gtctttggat    60
tataacttcg tataatgtat ggtatacgaa gttatttccc a                       101

<210>  SEQ ID NO  5
<211>  LENGTH: 83
<212>  TYPE: DNA
<213>  ORGANISM: Artificial <220>  FEATURE:
<223>  OTHER INFORMATION: a part of pUNO147 vector <400>  SEQUENCE: 5
tatacgaagt tatttcccct gcaggtcgac tctagaggat ccccgggaat tcagacatga    60
taagatacat tgatgagttt gga                                           83
```

UNITED STATES PATENT AND TRADEMARK OFFICE
CERTIFICATE OF CORRECTION

PATENT NO.       : 7,504,492 B2
APPLICATION NO.  : 10/545946
DATED            : March 17, 2009
INVENTOR(S)      : Hiroyuki Ueno et al.

It is certified that error appears in the above-identified patent and that said Letters Patent is hereby corrected as shown below:

```
<210> SEQ ID NO 6
<211> LENGTH: 83
<212> TYPE: DNA
<213> ORGANISM: Artificial
<220> FEATURE:
<223> OTHER INFORMATION: a part of pUNO149 vector
<400> SEQUENCE: 6
tatacgaagt tatttcccag ctctttctgg ctgcagtttt caagagaaac tgcagccaga    60
aagagctttt ttggatctgg ccg                                           83

<210> SEQ ID NO 7
<211> LENGTH: 83
<212> TYPE: DNA
<213> ORGANISM: Artificial

<220> FEATURE:
<223> OTHER INFORMATION: a part of pUNO148 vector

<400> SEQUENCE: 7
tatacgaagt tatttcccct gcaggtcgac tctagaggat ccccgggaat tcagacatga    60
taagatacat tgatgagttt gga                                           83
```

UNITED STATES PATENT AND TRADEMARK OFFICE
CERTIFICATE OF CORRECTION

PATENT NO. : 7,504,492 B2
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

```
<210>  SEQ ID NO  8
<211>  LENGTH:  83
<212>  TYPE:  DNA
<213>  ORGANISM:  Artificial <220>  FEATURE:
<223>  OTHER INFORMATION:  a part of pUNO150 vector <400>  SEQUENCE:  8
tatacgaagt tatttcccac ggccacaagt tcagcgtgtt caagagacac gctgaacttg    60
tggccgtttt ttggatctgg ccg                                           83

<210>  SEQ ID NO  9
<211>  LENGTH:  13
<212>  TYPE:  DNA
<213>  ORGANISM:  Artificial <220>  FEATURE:
<223>  OTHER INFORMATION:  a part of loxP <400>  SEQUENCE:  9
ataacttcgt ata                                                      13

<210>  SEQ ID NO  10
<211>  LENGTH:  29
<212>  TYPE:  DNA
<213>  ORGANISM:  Artificial <220>  FEATURE:
<223>  OTHER INFORMATION:  hH1/#3 primer <400>  SEQUENCE:  10
ggaattctta tagggagctg aagggaagg                                     29
```

UNITED STATES PATENT AND TRADEMARK OFFICE
CERTIFICATE OF CORRECTION

PATENT NO. : 7,504,492 B2
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

```
<210> SEQ ID NO 11
<211> LENGTH: 38
<212> TYPE: DNA
<213> ORGANISM: Artificial
<220> FEATURE:
<223> OTHER INFORMATION: hH1/#2 primer
<400> SEQUENCE: 11
gggatccgaa gactatggga aagagtggtc tcatacag                                 38

<210> SEQ ID NO 12
<211> LENGTH: 76
<212> TYPE: DNA
<213> ORGANISM: Artificial

<220> FEATURE:
<223> OTHER INFORMATION: HB-EGF_KO2 primer

<400> SEQUENCE: 12
cagggcccaa aaaagctctt tctggctgca gttctcttga aactgcagcc agaaagagct         60
gggaaagagt ggtctc                                                        76

<210> SEQ ID NO 13
<211> LENGTH: 29
<212> TYPE: DNA
<213> ORGANISM: Artificial

<220> FEATURE:
<223> OTHER INFORMATION: hH1/#5 primer

<400> SEQUENCE: 13
gctcgagtta tagggagctg aagggaagg                                          29
```

UNITED STATES PATENT AND TRADEMARK OFFICE
CERTIFICATE OF CORRECTION

PATENT NO.      : 7,504,492 B2
APPLICATION NO. : 10/545946
DATED           : March 17, 2009
INVENTOR(S)     : Hiroyuki Ueno et al.

It is certified that error appears in the above-identified patent and that said Letters Patent is hereby corrected as shown below:

```
<210>  SEQ ID NO  14
<211>  LENGTH:  118
<212>  TYPE:  DNA
<213>  ORGANISM:  Artificial <220>  FEATURE:
<223>  OTHER INFORMATION:  HLX primer <400>  SEQUENCE:  14
gggatccaaa aaagctcttt ctggctgcag tttctcttga aaactgcagc cagaaagagc    60
tgggaaataa cttcgtataa cagaacttat acgaagttat aatccaaaga catttcac    118

<210>  SEQ ID NO  15
<211>  LENGTH:  29
<212>  TYPE:  DNA
<213>  ORGANISM:  Artificial <220>  FEATURE:
<223>  OTHER INFORMATION:  hH1/#4 primer <400>  SEQUENCE:  15
gactagttta tagggagctg aagggaagg                                       29

<210>  SEQ ID NO  16
<211>  LENGTH:  27
<212>  TYPE:  DNA
<213>  ORGANISM:  Artificial <220>  FEATURE:
<223>  OTHER INFORMATION:  L/H primer <400>  SEQUENCE:  16
cctgcagggg aaataacttc gtataac                                         27
```

UNITED STATES PATENT AND TRADEMARK OFFICE
CERTIFICATE OF CORRECTION

PATENT NO. : 7,504,492 B2
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

```
<210> SEQ ID NO 17
<211> LENGTH: 30
<212> TYPE: DNA
<213> ORGANISM: Artificial
<220> FEATURE:
<223> OTHER INFORMATION: L-Sp primer
<400> SEQUENCE: 17
actagtcatg ataacttcgt ataagttctg                                          30

<210> SEQ ID NO 18
<211> LENGTH: 17
<212> TYPE: DNA
<213> ORGANISM: Artificial

<220> FEATURE:
<223> OTHER INFORMATION: M13 r primer

<400> SEQUENCE: 18
caggaaacag ctatgac                                                        17

<210> SEQ ID NO 19
<211> LENGTH: 65
<212> TYPE: DNA
<213> ORGANISM: Artificial

<220> FEATURE:
<223> OTHER INFORMATION: EGLX_(AS) oligomer

<400> SEQUENCE: 19
cgagatctaa aaaacggcca caagttcagc gtgtctcttg aacacgctga acttgtggcc         60
gtggg                                                                    65
```

UNITED STATES PATENT AND TRADEMARK OFFICE
CERTIFICATE OF CORRECTION

PATENT NO. : 7,504,492 B2
APPLICATION NO. : 10/545946
DATED : March 17, 2009
INVENTOR(S) : Hiroyuki Ueno et al.

It is certified that error appears in the above-identified patent and that said Letters Patent is hereby corrected as shown below:

```
<210> SEQ ID NO  20
<211> LENGTH:  64
<212> TYPE:  DNA
<213> ORGANISM:  Artificial
<220> FEATURE:
<223> OTHER INFORMATION:  EGLX_(S) oligomer
<400> SEQUENCE:  20
cgtcatgaat aacttcgtat aagttctgtt atacgaagtt atttcccacg gccacaagtt   60
cagc                                                                64

<210> SEQ ID NO  21
<211> LENGTH:  27
<212> TYPE:  DNA
<213> ORGANISM:  Artificial
<220> FEATURE:
<223> OTHER INFORMATION:  mU6/#1 primer
<400> SEQUENCE:  21
ggaattcatc cgacgccgcc atctcta                                       27

<210> SEQ ID NO  22
<211> LENGTH:  35
<212> TYPE:  DNA
<213> ORGANISM:  Artificial
<220> FEATURE:
<223> OTHER INFORMATION:  mU6/#2 primer
<400> SEQUENCE:  22
gggatccgaa gaccacaaac aaggcttttc tccaa                              35
```

UNITED STATES PATENT AND TRADEMARK OFFICE
CERTIFICATE OF CORRECTION

PATENT NO.        : 7,504,492 B2
APPLICATION NO.   : 10/545946
DATED             : March 17, 2009
INVENTOR(S)       : Hiroyuki Ueno et al.

It is certified that error appears in the above-identified patent and that said Letters Patent is hereby corrected as shown below:

```
<210>  SEQ ID NO  23
<211>  LENGTH:  75
<212>  TYPE:  DNA
<213>  ORGANISM:  Artificial <220>  FEATURE:
<223>  OTHER INFORMATION:  EGFP_KO1 primer <400>  SEQUENCE: 23
cggatccaaa aacggccaca agttcagcgt gtctcttgaa cacgctgaac ttgtggccga    60
aacaaggctt ttctc                                                    75

<210>  SEQ ID NO  24
<211>  LENGTH:  27
<212>  TYPE:  DNA
<213>  ORGANISM:  Artificial <220>  FEATURE:
<223>  OTHER INFORMATION:  mU6/#1 primer <400>  SEQUENCE: 24
ggaattcatc cgacgccgcc atctcta                                       27
```

UNITED STATES PATENT AND TRADEMARK OFFICE
CERTIFICATE OF CORRECTION

PATENT NO.          : 7,504,492 B2
APPLICATION NO. : 10/545946
DATED                  : March 17, 2009
INVENTOR(S)        : Hiroyuki Ueno et al.

It is certified that error appears in the above-identified patent and that said Letters Patent is hereby corrected as shown below:

```
<210>  SEQ ID NO  25
<211>  LENGTH:  17
<212>  TYPE:  DNA
<213>  ORGANISM:  Artificial <220>  FEATURE:
<223>  OTHER INFORMATION:  M13 (-20) Forward primer <400>  SEQUENCE:  25
gtaaaacgac ggccagt                                                      17 --
```

Signed and Sealed this

Ninth Day of June, 2009

JOHN DOLL
*Acting Director of the United States Patent and Trademark Office*